United States Patent
Tomoda et al.

(10) Patent No.: US 7,379,573 B2
(45) Date of Patent: May 27, 2008

(54) METHOD AND APPARATUS FOR PROCESSING IMAGES USING THREE-DIMENSIONAL ROI

(75) Inventors: Yukihiko Tomoda, Otawara (JP); Naoyuki Furudate, Otawara (JP)

(73) Assignee: Kbushiki Kaisha Toshiba, Tokyo (JP)

( * ) Notice: Subject to any disclaimer, the term of this patent is extended or adjusted under 35 U.S.C. 154(b) by 159 days.

(21) Appl. No.: 10/638,473

(22) Filed: Aug. 12, 2003

(65) Prior Publication Data
US 2004/0059214 A1    Mar. 25, 2004

(30) Foreign Application Priority Data
Aug. 13, 2002  (JP) ............... 2002-235823

(51) Int. Cl.
*G06K 9/00*    (2006.01)
(52) U.S. Cl. ............ 382/128; 382/132; 600/407; 600/410
(58) Field of Classification Search .......... 600/407, 600/410; 382/128, 132
See application file for complete search history.

(56) References Cited

U.S. PATENT DOCUMENTS

| | | | | |
|---|---|---|---|---|
| 5,514,957 A | * | 5/1996 | Tatebayashi | 324/309 |
| 5,545,993 A | * | 8/1996 | Taguchi et al. | 324/309 |
| 6,396,897 B1 | * | 5/2002 | Ebrahimifard et al. | 378/4 |
| 6,720,966 B2 | * | 4/2004 | Barth et al. | 345/424 |
| 6,721,590 B2 | * | 4/2004 | Ohishi et al. | 600/431 |

FOREIGN PATENT DOCUMENTS

| | | |
|---|---|---|
| JP | 3-251971 | 11/1991 |
| JP | 6-217958 | 8/1994 |
| JP | 8-212391 | 8/1996 |
| JP | 11-9590 | 1/1999 |
| JP | 2001-22964 | 1/2001 |
| JP | 2001-52195 | 2/2001 |
| JP | 2001-118086 | 4/2001 |

* cited by examiner

*Primary Examiner*—Brian L. Casler
*Assistant Examiner*—John F. Ramirez
(74) *Attorney, Agent, or Firm*—Nixon & Vanderhye P.C.

(57) ABSTRACT

A plurality of images of a plurality of sections in an object are processed by using a ROI-specifying unit to specify a three-dimensional (3D) ROI (region of interest) at a region to be targeted in a three-dimensional space formed by the images. A deciding unit is then used to select one or more sections crossing the three-dimensional ROI, and a display unit is used to display images of the selected sections. The image of each of the selected sections includes an area crossing the 3D ROI. The ROI-specifying unit operates to place the 3D ROI at a region to be targeted on a first image of a section and three-dimensionally locates the 3D ROI at the region to be targeted by using both the first image and a second image of another section.

38 Claims, 9 Drawing Sheets

METHOD AND APPARATUS FOR PROCESSING IMAGES USING THREE-DIMENSIONAL ROI

BACKGROUND OF THE INVENTION

1. Technical Field of the Invention

The present invention relates to a method and apparatus for processing a plurality of sectional images of an object to be diagnosed with the use of a three-dimensional ROI (region of interest) such as spherical ROI.

2. Description of Related Art

Recently, medical imaging modalities, such as X-ray CT scanners and MRI (magnetic resonance imaging) systems, have become popular in medical facilities in which medical diagnosis and treatment is actually performed. Such medical imaging modalities are able to easily produce a large quantity of images of each patient (i.e., object to be diagnosed) in the course of medically examining or treating the patient.

For example, the MRI system has the capability of acquiring a large number of images of a patient by using a magnetic resonance imaging technique. With this technique, nuclear spins in an object placed in a static magnetic field are magnetically excited by an RF signal of a Larmor frequency of the nuclear spins. This excitement makes it possible that an MR signal emanated from the object due to the excitation is acquired and an image is reconstructed using the MR signal.

For imaging various sections of a patient using the magnetic resonance imaging, the direction of each section can be decided freely and the same region within the patient can be imaged in various different directions. Thus, this imaging capability will easily produce, if necessary, a large number of images in the process of diagnosing each patient. For a doctor's comparative observation of images, there has been a demand that the same region to be imaged be clearly pointed out on each of a plurality of images, when the images are displayed. Conventionally, this pointing-out function has been realized in various ways, such as by presentation of one or more mutual relationships between or among sections that have been imaged or by presentation of positional information about images to be displayed.

However, the conventional pointing-out techniques are not sufficient for easily and precisely supplying positional information about the same imaged region among plural sectional images. To be specific, though the same region is depicted in various sectional images, understanding where the region on any sectional image is located on the other sectional images is rather difficult for doctors or others. The reason is that, since various sections different imaging directions may also be imaged differently from each other, whereby an offset of each section is changed subtly. Such a difficulty is not limited to MRI systems, but is also true of X-ray CT scanner systems.

SUMMARY OF THE INVENTION

The exemplary embodiments of the present invention has been created in consideration of the above described drawbacks of conventional image processing. An object of the present exemplary embodiments is to provide method and apparatus for processing images, which are able to easily and precisely provide image information helpful for understanding where a desired region specified on any sectional image is located on other sectional images and how such desired region is displayed on the other sectional images.

In the present exemplary embodiments, there is provided an image processing apparatus and an image processing method, which can be integrated into medical imaging modalities, such as X-ray CT scanner and MRI systems or can be reduced to practice as a stand-alone system, separately from those modalities. separately from those modalities.

An image processing apparatus and image processing method according to an exemplary embodiment involves the specification of a ROI (region of interest) structured three-dimensionally (hereinafter, this ROI is referred to as a "three-dimensional (3D) ROI"). This 3D ROI is used for providing, as one mode of the present invention, a function of specifying the medically desired same region in both the image of an arbitrary section (i.e., a tomographic image) and the image of another section of the same object to be diagnosed and a function of searching and displaying other sections crossing the 3D ROI.

A 3D ROI of any body shape, such as a spherical body, elliptical body, column-like body, tetrahedron-like body, or circular-cone-like body (fixed shape) can be used. In contrast, a 3D ROI of which body shape is not fixed beforehand may also be used. Such a non-fixed shape 3D ROI is set up, for example, by combining various types of polygons. Preferably, some 3D ROIs having typical shapes are previously chosen and registered in a memory, so that a 3D ROI can be selected according to the contour of a region to be observed in terms of medical examination or treatment.

The sectional images used in the exemplary embodiments, which compose a 3D image, includes an axial image of a section (axial plane) perpendicular to the body axis of an object (patient), coronal image of a section (coronal plane) perpendicular to the axial plane but in parallel with the front of the object body, sagittal image of a section (sagittal plane) perpendicular to both the axial plane and the coronal plane, and oblique image of an oblique plane other than the axial, coronal and sagittal planes.

In order to realize the foregoing object, the present exemplary embodiments provides, as one aspect thereof, an apparatus for processing a plurality of images of a plurality of sections in an object to be diagnosed. The apparatus comprises a ROI-specifying unit configured to specify a three-dimensional ROI (region of interest) at a region to be targeted in a three-dimensional space formed by the plurality of images; a specifying unit configured to specify one or more sections of the plurality of sections crossing the three-dimensional ROI; and a display unit configured to display images of the sections decided by the deciding unit.

Preferably, the display unit is configured to display the images of the sections decided by the deciding unit, the image of each of the decided sections including an area crossing the three-dimensional ROI being superposed on each image.

By way of example, the display unit comprises a unit configured to search the plurality of sections for sections crossing the three-dimensional ROI and to decide a contour of the area crossing the three-dimensional ROI in each of the decided section.

It is also preferred that the ROI-specifying unit comprises a ROI-placing unit configured to place the three-dimensional ROI at a region to be targeted on a first image of a section selected from the plurality of sections; and a ROI-locating unit configured to three-dimensionally locate the thee-dimensional ROI at the region to be targeted by using both the first image and a second image of another section from the plurality of sections.

It is still preferred that the three-dimensional ROI is a spherical ROI. Further, the apparatus can be functionally incorporated in a medical imaging modality for acquiring the plurality of images at the plurality of sections. By way of example, the medical imaging modality is an MRI (magnetic resonance imaging) system or an X-ray CT (computed tomography) scanner.

As another aspect of the present invention, there is provided a method for processing a plurality of images of a plurality of sections in an object to be diagnosed, the method comprising the steps of: placing a three-dimensional ROI (region of interest) at a region to be targeted on a first image of a section selected from the plurality of sections; three-dimensionally locating the thee-dimensional ROI at the region to be targeted by using both the first image and a second image of another section from the plurality of sections; specifying one or more sections of the plurality of sections crossing the three-dimensional ROI; and displaying images of the sections decided by the deciding step.

By way of example, the display step is configured to display the images of the sections decided by the deciding step, the image of each of the decided sections including an area crossing the three-dimensional ROI being superposed on each image. It is preferred that the display step comprises the sub-steps of: searching the plurality of sections for sections crossing the three-dimensional ROI; and deciding a contour of the area crossing the three-dimensional ROI in each of the decided section.

Still another aspect of the present invention, there is provided a program executed by a computer for processing a plurality of images of a plurality of sections in an object to be diagnosed, the program enabling the computer to have the functions of: placing a three-dimensional ROI (region of interest) at a region to be targeted on a first image of a section selected from the plurality of sections; three-dimensionally locating the thee-dimensional ROI at the region to be targeted by using both the first image and a second image of another section from the plurality of sections; specifying one or more sections of the plurality of sections crossing the three-dimensional ROI; and displaying images of the sections decided by the deciding step.

As a result, applying the 3D ROI to 3D image data according to the above explained manner make it possible that sections crossing the 3D ROI can be determined and an area of each crossing section, which is contained in the 3D ROI, can be displayed. Hence the same region to be targeted, which is marked by the 3D ROI, can be displayed in the plural images for comparative observation. The region to be targeted can therefore be observed in a strengthened manner. In addition, applying the 3D ROI to 3D image data acquired from the same object (patient) will enable images crossing the 3D ROI to be searched and displayed automatically by the apparatus. Therefore, compared to the conventional manner, the same lesion of the same patient can be observed easily and steadily using a plurality of images acquired from the patient.

DETAILED DESCRIPTION OF PREFERRED EMBODIMENTS

Referring to the accompanying drawings, preferred embodiments of a method and apparatus for processing medical images will now be explained.

(First Embodiment)

Referring to FIGS. 1 to 5, a first embodiment of the present invention will now be described.

Figure 1:
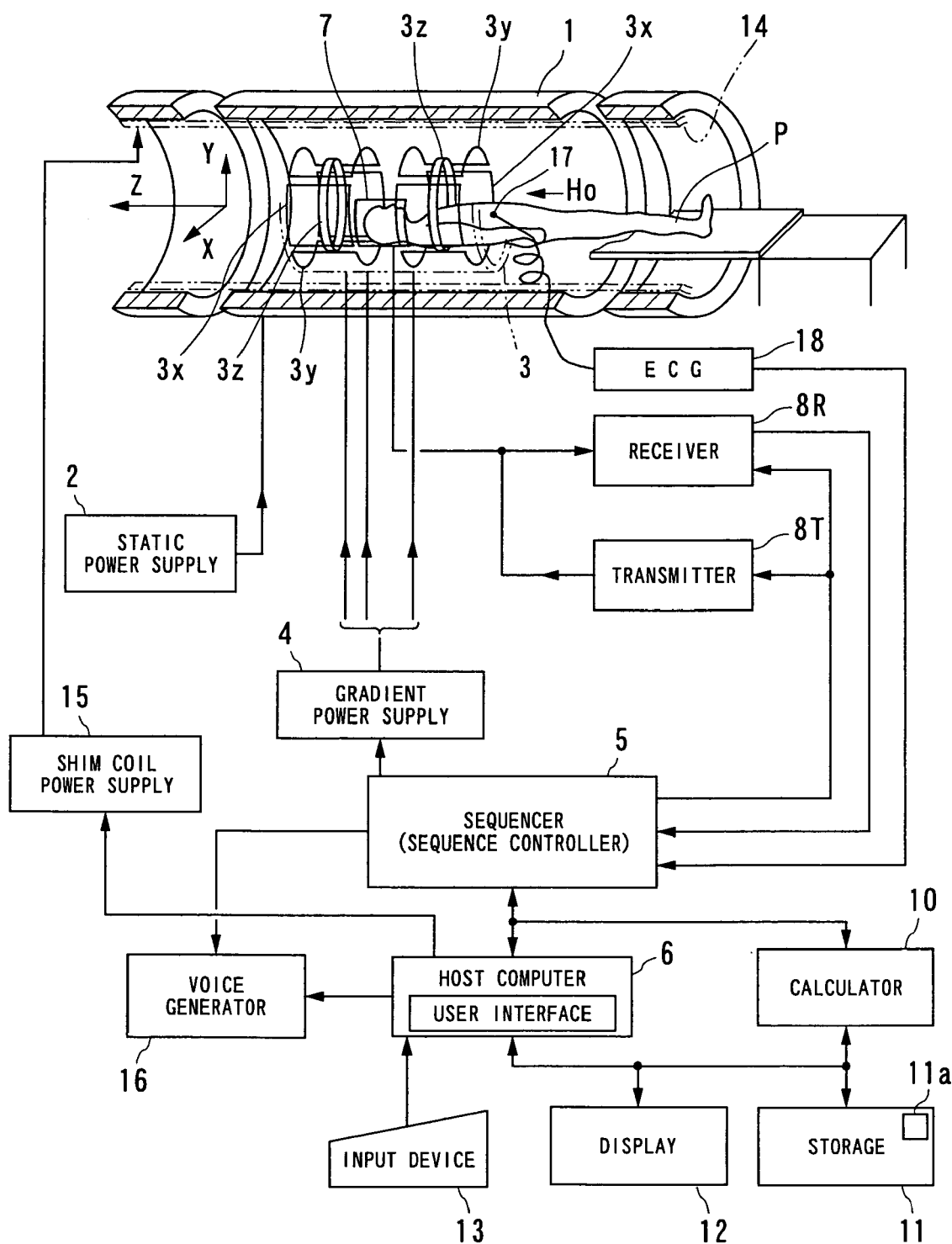
FIG. 1 shows a block diagram of an MRI (magnetic resonance imaging) system serving as the medical imaging modality according to the present invention, the medical imaging modality functionally including an image processing apparatus according to a first embodiment of the present invention.

An MRI (magnetic resonance imaging) system used in this embodiment is outlined in FIG. 1. This MRI system has been exemplified as just one type of medical imaging modalities that functionally includes the image processing apparatus according to the present invention.

The MRI system comprises a patient couch on which a patient (object to be examined) P lies down on its couch top, static field generating components for generating a static magnetic field, gradient generating components for appending positional information to the static magnetic field, transmitting/receiving components for transmitting and receiving radio-frequency signals, controlling and calculating components responsible for control of the whole system and reconstruction of images, electrocardiographing components for acquiring an ECG signal which is a representative signal indicative of the cardiac temporal phase of a patient, and breath-hold instructing components for instructing the patient to temporarily hold his or her breath.

The static field generating components includes a magnet 1 that is of, for example, a superconducting type, and a static power supply 2 for supplying a current to the magnet 1, and generates a static magnetic field $H_0$ in an axial direction (Z-axis direction) in a cylindrical bore (diagnostic space) into which a patient P is inserted. The magnet unit is provided with shim coils 14. A current used to homogenize a static magnetic field is supplied from a shim coil power supply 15 to the shim coils 14 under the control of a host computer to be described later. The couch top of the patient couch on which the patient P lies down can be inserted into the bore of the magnet 1 so that the couch top can be withdrawn therefrom.

The gradient generating components has a gradient coil unit 3 incorporated in the magnet 1. The gradient coil unit 3 comprises three pairs (kinds) of x-, y-, and z-coils $3x$ to $3z$ used to generate gradients (magnetic field gradients) changing in strength in predetermined physical X-axis, Y-axis, and Z-axis directions that are mutually orthogonal. The gradient generating components further include a gradient power supply 4 for supplying pulsed currents to the x-, y-, and z-coils $3x$ to $3z$ to generate pulsed gradients under the control of a sequencer 5 that will be described later.

The pulsed currents supplied from the gradient power supply 4 to the x-, y-, and z-coils $3x$ to $3z$ are controlled, whereby gradients in the three physical X-, Y-, and Z-directions are synthesized arbitrarily. Thus, logical axial directions consisting of directions of a slice gradient $G_S$, a phase-encoding gradient $G_E$, and a readout (frequency-encoding) gradient $G_R$ can be specified and changed arbitrarily. The gradients to be applied individually in the slice direction, phase-encoding direction, and readout direction are superposed on the static magnetic field $H_0$.

The transmitting/receiving components comprises not merely an RF coil 7 located in the vicinity of a patient P in the bore inside the magnet 1 but also a transmitter 8T and a receiver 8R both electrically connected to the coil 7, which operate under the control of a sequencer 5 described later. The transmitter 8T supplies to the RF coil 7 pulsed RF currents of a Larmor frequency to excite spins to cause a nuclear magnetic resonance (NMR) phenomenon. The receiver 8R takes in MR signals (such as echo signals composed of RF signals) that the RF coil 7 has received, carries out various kinds of signal processing with the MR signals, such as pre-amplification, intermediate-frequency conversion, phase detection, lower-frequency amplification, and specified types of filtering, and A/D-converts the processed MR signals with produced digital data (i.e., original raw data).

The control and calculation components include a sequencer 5 (frequently referred to as sequence controller), a host computer 6, calculator 10, storage 11, display 12, input device 13, and voice generator 16. Of these, the host computer 6 has the function of providing the sequencer 5 with pieces of information based on a pulse sequence and managing the operations of the entire system according to previously installed software programs.

The host computer 6, which has a CPU and incorporated memories, commands the entire system to carry out an imaging scan based on a predetermined pulse sequence. The imaging scan carried out in this embodiment is, for instance, a multi-slice scan. In addition, the host computer 6 serves as the main part of an interactive user interface (UI) during a scanning plan. Specifically, the host computer 6 functionally establishes the user interface with the help of both the display 12 and the input device 13. The user interface is therefore able to not only receive necessary information about both scanning and image post-processing from an operator but also provide the operator with acquired and post-processed images or others.

The sequencer 5, which has a CPU and memories, stores pulse sequence information sent from the host computer 6, and controls the operations performed by the gradient power supply 4, transmitter 8T, and receiver 8R according to the stored information. Additionally the sequencer 5 temporarily receives digital data corresponding to MR signals outputted from the receiver 8R, before transferring them to the calculator 10. The pulse sequence information is made up of all pieces of information required for operating the gradient power supply 4, transmitter 8T, and receiver 8R according to a series of pulses consisting of a pulse sequence. This pulse sequence information therefore includes information on the strength, duration, and application timing of pulsed currents applied to the x-, y-, and z-coil $3x$ to $3z$.

The calculator 10 receives digital echo data sent from the receiver 8R via the sequencer 5, maps the received data in a Fourier space (known as a k-space or frequency space) formed in its incorporated memory, and performs a two-dimensional or a three-dimensional Fourier transform with the mapped data so as to reconstruct an image in the real space. Moreover, the calculator 10 also carries out such processing as synthesis and difference calculation of image data.

The storage 11 has a memory that can preserve not merely reconstructed image data but also image data that have undergone various types of processing such as synthesis and difference calculation. The storage unit 11 has a computer-readable recording medium $11a$, such as ROM or disk, into which program data indicative of a desired type of pulse sequence according to the present invention is recorded. The program data recorded in the recording medium $11a$ of the storage 11 is read out therefrom in response to a command issued by the host computer 6, and then sent to the sequencer 5 via the host computer 6.

The display 12 displays an image. The input device 13 is used by an operator to provide the host computer 6 with desired imaging conditions, a desired pulse sequence, and information about image synthesis and/or difference calculation.

Further, the breath-hold instructing components have a voice generator 16 as its one constituent. When receiving a command from the host computer 6, the voice generator 16 utters voice or massages or sound which requests the start and end of patient's temporal breath hold. Accordingly, a temporal breath hold for a predetermined scan time is instructed toward the patient P.

Moreover, the electrocardiographing components comprises an ECG sensor 17 attached to the object's body to detect an electronic ECG signal and an ECG unit 18 performing various type of processing including digitization on the detected ECG signal, so that the processed ECG signal is sent to both the host computer 6 and the sequencer 5. This ECG signal is used, for example, by the sequencer 5 to perform an ECG-gating (electrocardiographing synchronization) imaging scan. This enables an appropriate determination of synchronous timing on the ECG-gating technique, whereby an imaging scan on the ECG-gating technique can be performed well to acquire data.

Referring to FIGS. 2 to 5, how to specify a three-dimensional desired region in images according to the present embodiment, which is carried out after acquisition of images, will now be described.

This region specifying technique is required to define a three-dimensional (3D) ROI (region of interest), to use the 3D ROI to specify the same desired region between in an arbitrary sectional image (for example, an axial, coronal, sagittal or oblique image) and in another sectional image, to automatically search sections crossing the 3D ROI, and to display the images of the searched sections. In this example of the MRI system shown in FIG. 1, this region-specifying technique can be realized by the user interface functionally configured by the host computer 6, display 12, and input device 13.

Figure 2:
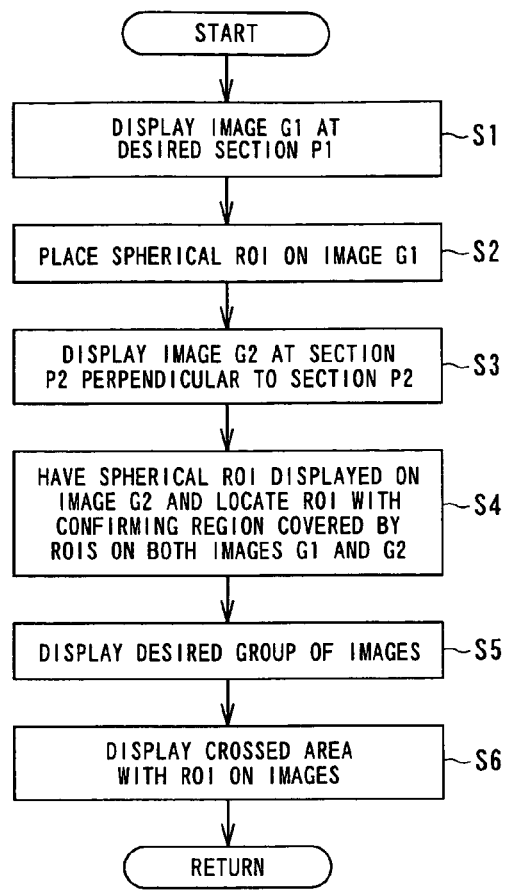
FIG. 2 is a flowchart outlining the processing for specifying a region in images, the processing being carried out in the first embodiment.

The region specifying technique is conducted according to the procedures shown by a flow outlined in FIG. 2. As shown therein, first of all, of plural sections of a patient P which are set to include a desired region to be diagnosed of a patient P (for example, the head) and acquired under, for example, a multi-slice technique by the MRI system, an arbitrary section P1 is specified in response to a user's operation performed at the input device 13, with the result that an image G1 of the section P1 is displayed at a predetermined position on a screen of the display 12 (step S1).

Figure 3:
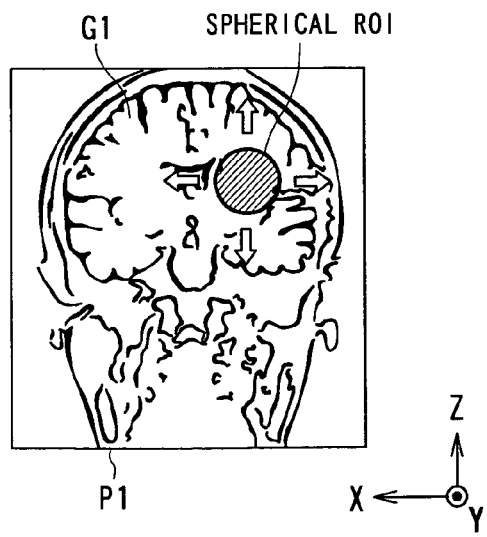
FIG. 3 exemplifies an image displayed through the processing at steps S1 and S2 of the region-specifying processing in FIG. 2, the image including a spherical ROI (region of interest) specified.

FIG. 3 exemplifies such image G1. In this exemplification, the image G1 of an arbitrary section P1 is an image of a plane in parallel with the ZX plane, that is, a coronal image (a portion to be diagnosed is the head). In the following, this image G1 of the coronal plane P1 will be explained.

A three-dimensional ROI (hereafter referred to as "spherical ROI") defined by specifying both a desired radius and a central position) is then set on the image G1 of the coronal plane P1 (step S2). The spherical ROI can be designated such that an operator, who views the display 12 on which markers such as arrows are placed on its screen, operates the input device 13 to move the markers or others so that parameters about the spherical ROI are designated in an intuitive manner. The parameters are composed of a central position $(X_0, Y_0, Z_0)$ and a radius R in a virtual three-dimensional space (XYZ coordinate space) made up of plural sections.

Figure 4:
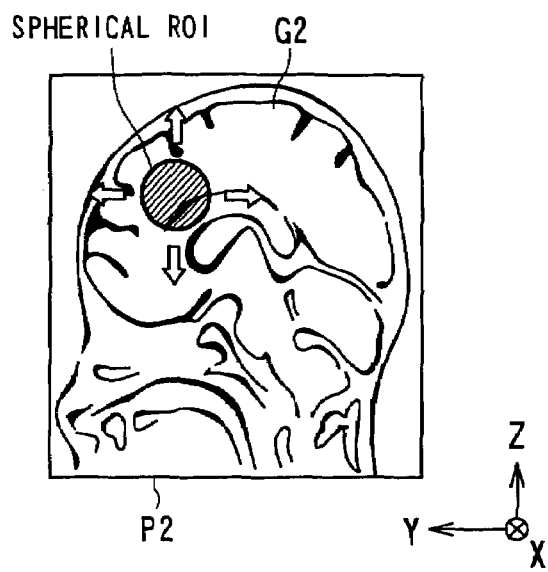
FIG. 4 exemplifies an image used for positioning the spherical ROI, together with the image shown in FIG. 3, through the processing at steps S3 and S4 in FIG. 2, the image including the spherical ROI.
Figure 5:
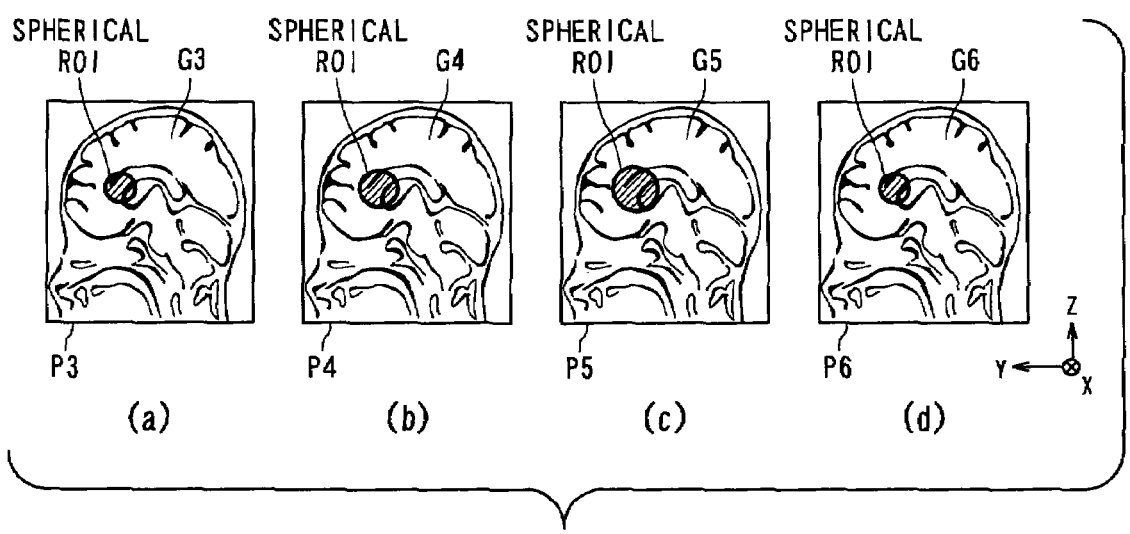
FIG. 5 exemplifies plural images displayed through the processing at steps S5 and S6 in FIG. 2, the images each including the spherical ROI.

In addition to the image G1 of the coronal plan P1, as shown in FIG. 4, an patient's head image G2 of a section perpendicular to the plane P1, which is for example a YZ plane (sagittal plane) P2, is then displayed at another predetermined position on the screen of the display 12 (step S3). In this display, the spherical ROI that has already been designated on the image G1 of the coronal plane P1 is also displayed on the image G2 of the sagittal plane in a superposed manner. Thus, while the operator observes the state of region of the spherical ROI (i.e., its position and size) displayed on both the image G1 of the coronal plane P1 shown in FIG. 3 and the image G2 of the sagittal plane P2 shown in FIG. 4, the operator operates the input device 13 to locate the spherical ROI at a target region to be diagnosed (step S4).

After completing the location of the spherical ROI, the operator again operates the input device 13 to specify and display a desired group of images, for instance, four images of arbitrary four sections (sagittal planes along the YZ plane) shown in FIG. 5(a) to (d) (step S5). In this specification and display, if the four sections include areas crossing the spherical ROI already designated, such crossed areas are also displayed on the images shown in (a) to (d) of FIG. 5 in a superposed manner, respectively (step S6). The determination whether or not each section (plane) to be displayed crosses the spherical ROI so as to form a crossed region is carried out based on both a spherical equation determined by a central position of the spherical ROI and a radius thereof and a plane equation determined by an arbitrary position in a section of which image is desired and parameters showing a normal vector perpendicular to the section.

Accordingly, the present embodiment is able to deal with a plurality of sections that have been subjected to imaging of the same patient's region in different directions. That is, one or more sections that cross the spherical ROI can be displayed as sectional images in which regions crossing the spherical ROI are depicted. Hence it is possible for a doctor or others to easily recognize that a region specified on a desired sectional image is located at which part on each of other sectional images, i.e., the same selected region is located at which part on each of plural images. This is effective in enhancing efficiency of interpretation of images.

(Second Embodiment)

Referring to FIGS. 6 to 10, a second embodiment of the present invention will now be explained. This embodiment is different from the processing procedures shown in FIG. 2 in steps S5 and S6 among the entire steps S1 to S6. The processing for this second embodiment will now be exemplified with reference to FIG. 6.

Figure 6:
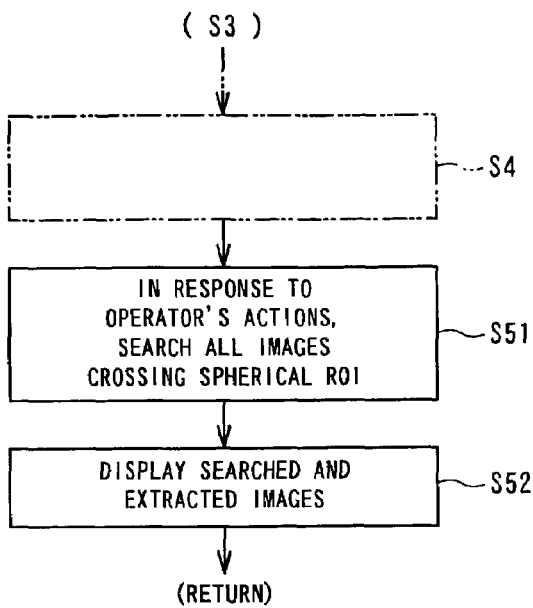
FIG. 6 is a partly shown flowchart outlining the processing for specifying a region in images in accordance with a second embodiment of the present invention.

In the processing shown in. FIG. 6, coronal images of a patient's head portion will be exemplified like the foregoing embodiment. Using the image G1 of the coronal plane P1 (refer to FIG. 3) and the image G2 of the sagittal plane P1 (refer to FIG. 4), the spherical ROI is specified at a desired location (step S4). In response to operator's actions (operations done at the input device 13), all images of all sections that cross the specified and located spherical ROI are then automatically searched and extracted from all the images that have already been imaged about the same patient (step S51). These images, from which images crossing the spherical ROI are extracted, include images acquired by the MRI system and if available, images of the same patient acquired by other medical imaging modalities such as X-ray CT scanner and delivered through a communication network. Thus, the present embodiment can be applied to a PACS (Picture Archiving and Communication Systems).

Figure 7:
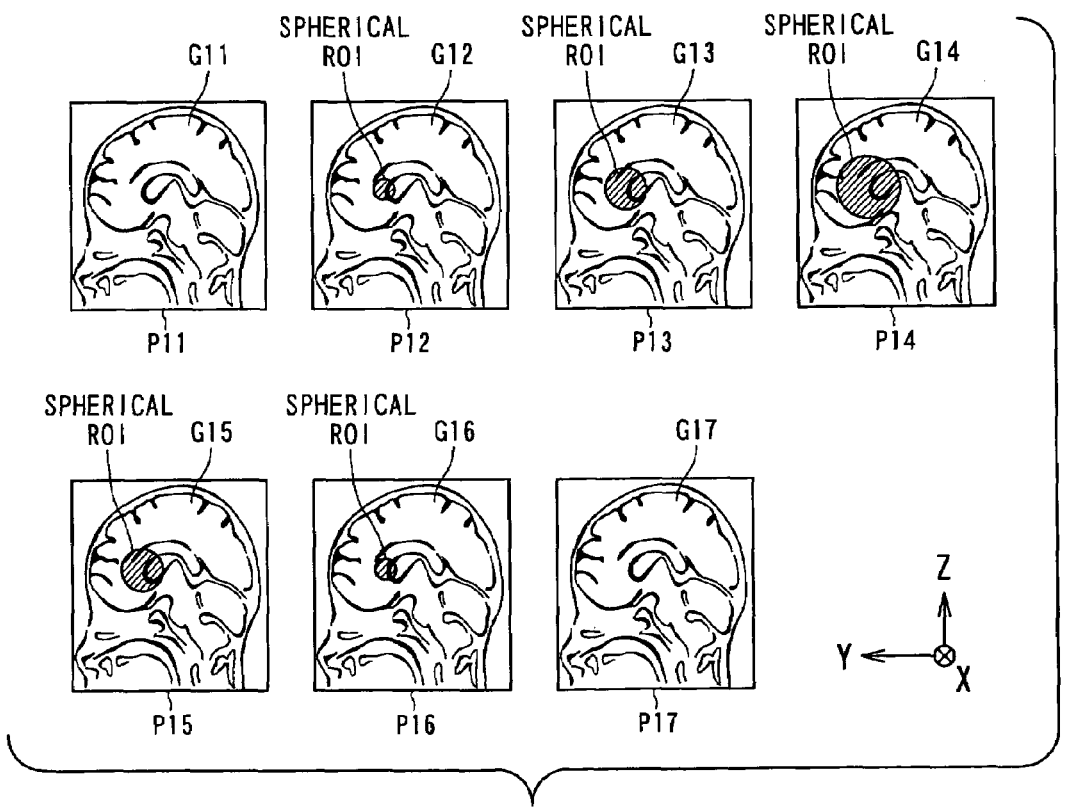
FIG. 7 exemplifies sagittal images extracted and displayed at steps S51 and S52 in FIG. 6.
Figure 8:
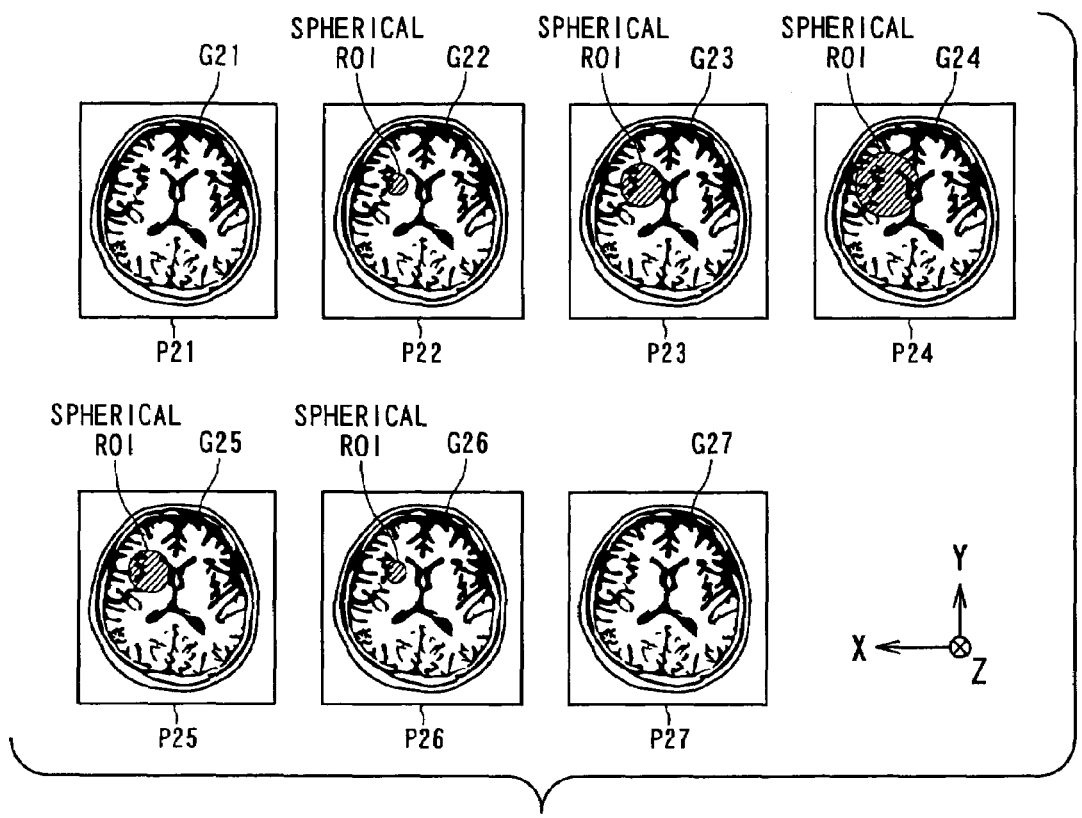
FIG. 8 exemplifies axial images extracted and displayed at steps S51 and S52 in FIG. 6.

All the extracted images are displayed on the screen of the display 12 (step S52). Display examples of such extracted images are shown in FIGS. 7 and 8, respectively. The positional relationships between those sections and the spherical ROI are shown in FIGS. 9A and 9B to 10A and 10B, respectively.

Figure 9A:
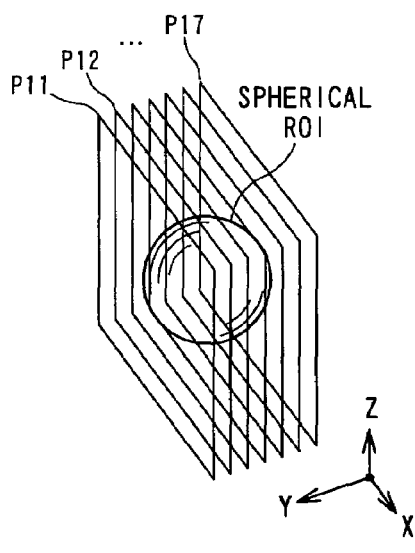
FIGS. 9A and 9B explain the positional relationship between the sagittal planes in FIG. 7 and the spherical ROI.
Figure 9B:
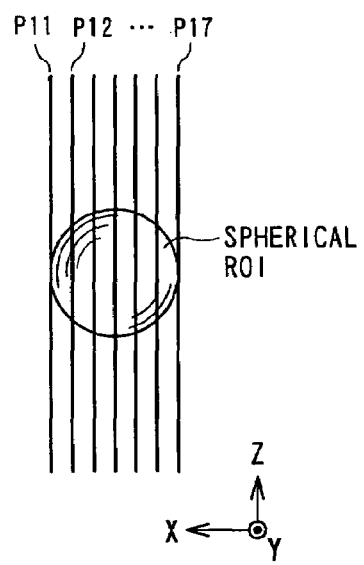
Figure 10A:
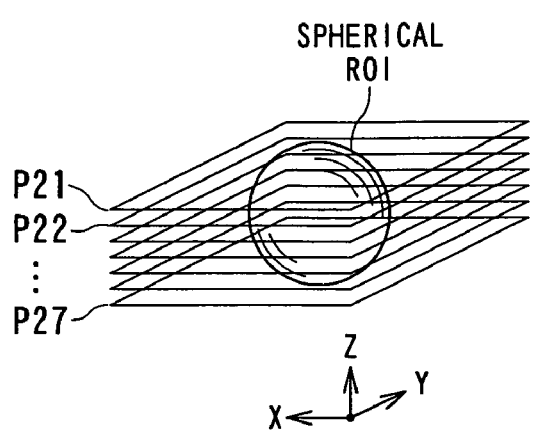
FIGS. 10A and 10B explain the positional relationship between the sagittal planes in FIG. 7 and the spherical ROI.
Figure 10B:
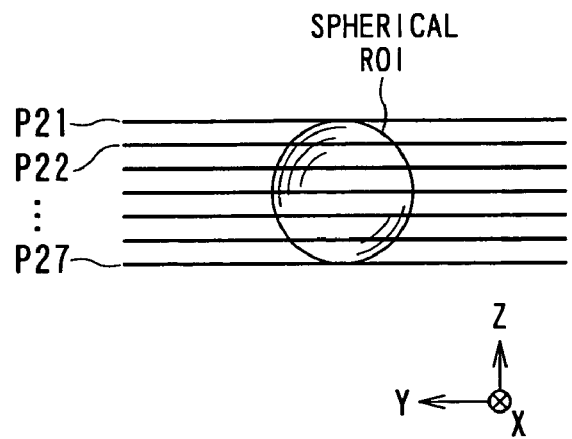

The extracted images shown in FIG. 7, which show a patient's head, consist of seven images P11 to P17 of seven sagittal planes (YZ planes) crossing the spherical ROI, of which positional relationship between the sagittal planes P11 to P17 and the spherical ROI are shown in FIGS. 9A and 9B. Similarly to the above, the extracted images shown in FIG. 8, which show a patient's head, consist of seven images P21 to P27 of seven axial planes (XY planes) crossing the spherical ROI, of which positional relationship between the axial planes P21 to P27 and the spherical ROI are shown in FIGS. 10A and 10B.

Thus, in addition to the operations and advantages obtained in the first embodiment, images which cross the spherical ROI can be searched and displayed from the same patient's images previously acquired and stored in a memory unit. As a result, when locating the spherical ROI at a lesion to be diagnosed, the same patient's lesion is allowed to be observed in different images in a simpler and steadier manner than the conventional.

(Third Embodiment)

Figure 11:
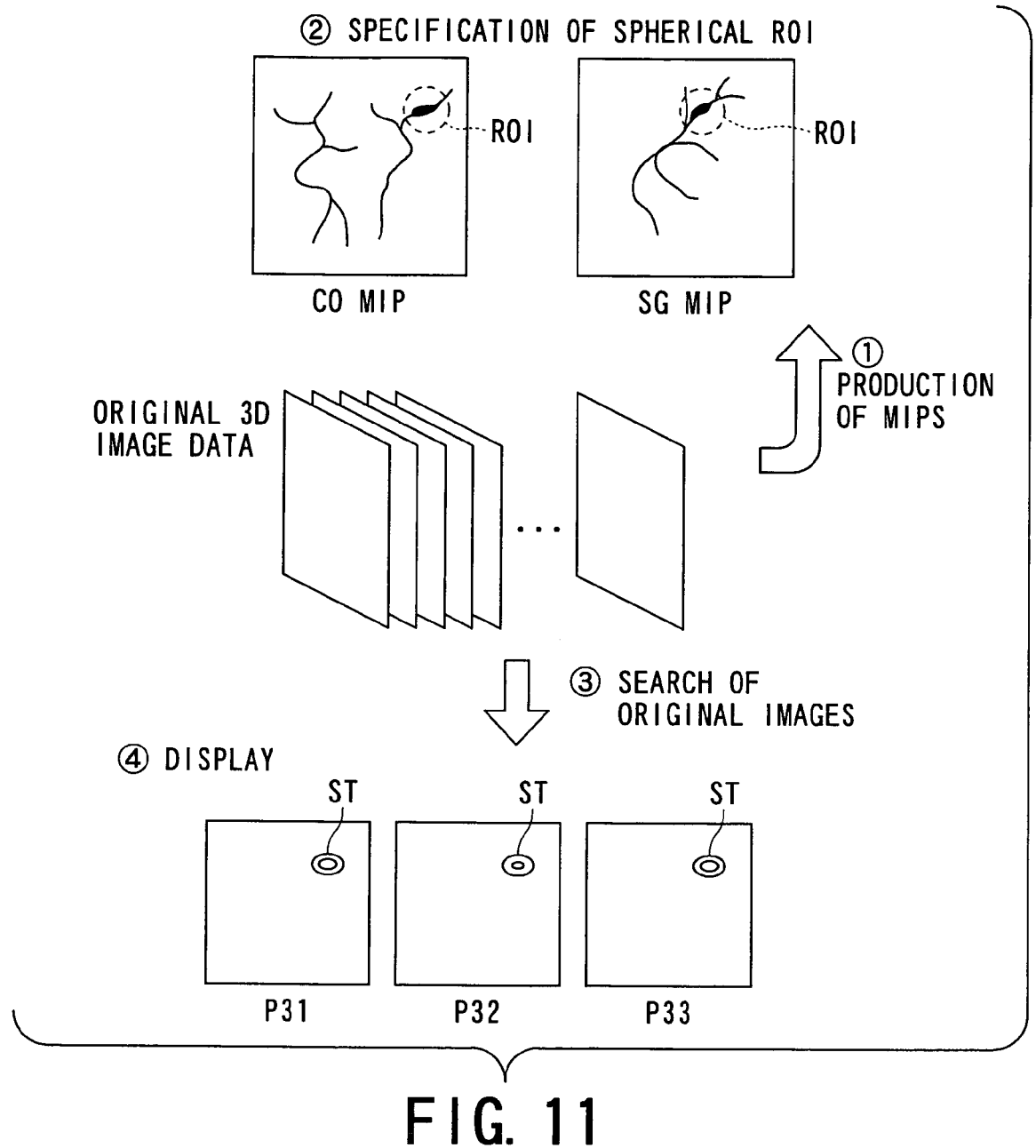
FIG. 11 an illustration explaining the processing for searching images by using a three-dimensional ROI, which is carried out in a third embodiment of the present invention.
Figure 12:
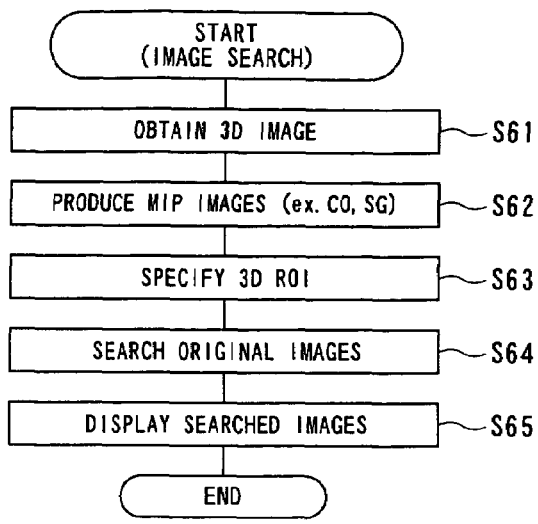
FIG. 12 is a flowchart outlining the processing according to the third embodiment.

Referring to FIGS. 11 and 12, a third embodiment of the present invention will now be described. This embodiment concerns with specifying a three-dimensional ROI in MIP (maximum intensity projection) images and searching images based on the ROI. In the present and subsequent embodiments, the MRI system, serving as one type of the medical imaging modalities according to the present invention, is constructed in the same way as the first embodiment.

FIG. 11 explains how to process original images in the present embodiment, while FIG. 12 shows an outlined flow of processing carried out using the user interface (i.e., the host computer 6, display 12, and input device 13).

First, in response to an operator's command, the host computer 6 operates such that three-dimensional (3D) image data is obtained by actually scanning an object P (patient) in, for example, a multi-slice technique or reading out 3D image data that has already been acquired and stored in the storage 11 or other memory means (step S61 in FIG. 12). This 3D image data, composed of data of a plurality of sections, is temporarily stored as original 3D image data in a work area of the host computer 6.

By the host computer 6, two kinds of MIP images (two-dimensional images) are then produced from the original 3D image data. As shown in FIG. 11, the MIP images are for example coronal and sagittal MIP images of the object P (step S62). In these MIP images, through the user interface, a spherical ROI serving as the three-dimensional ROI is specified (placed and located) at a desired region in the similar way to that in the foregoing embodiments (step S63). The spherical ROI is placed and located, for instance, at a stenosed part (or doubtful part about a stenosis) of a blood vessel depicted in the MIP images.

After this, from the original 3D images, one or more sections that across the specified spherical ROI are searched, and their sectional images are displayed (steps S64 and S65). Hence, by way of example, three sectional images P31 to P33 are selected from the original 3D image composed of images of 2D plural sections and subjected to the display on the screen of the display 12 (refer to FIG. 11).

As a result, sections of the targeted stenosis part ST of a blood vessel or blood vessel which is doubtful about the stenosis are depicted in those finally searched sectional images. It is therefore possible to find necessary sectional images from a large volume of images as quickly as possible by using the three-dimensional ROI, and to easily draw a comparison between the MIP images and the original images in diagnosis. This is a great help for a doctor who should observe or interpret images, thus providing an easy-to-use user-aiding system in observing large number of images.

(Fourth Embodiment)

Figure 13:
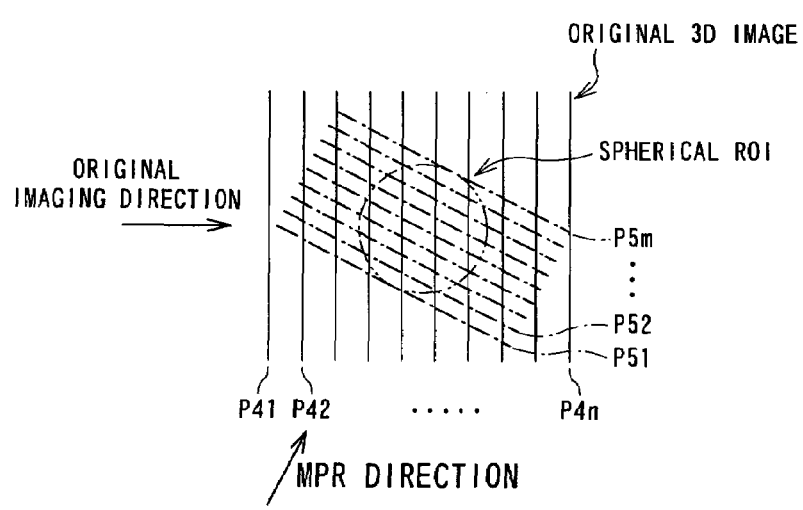
FIG. 13 an illustration explaining the processing for producing images by using a three-dimensional ROI, which is carried out in a fourth embodiment of the present invention.
Figure 13:
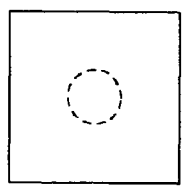
Figure 13:
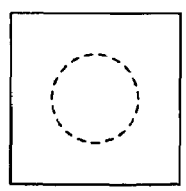
Figure 13:
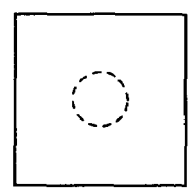
Figure 14:
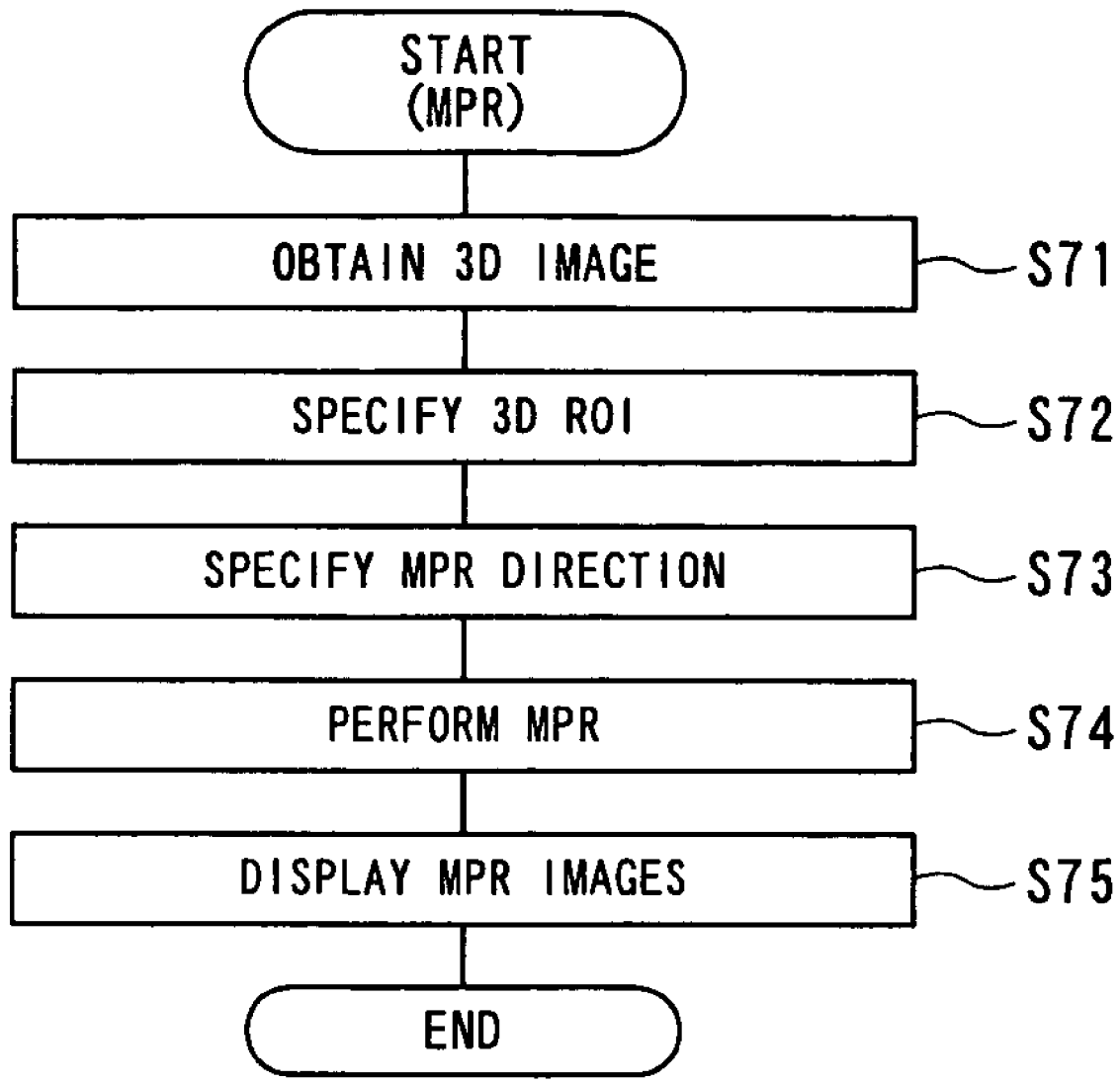
FIG. 14 is a flowchart outlining the processing according to the fourth embodiment.

Referring to FIGS. 13 and 14, a fourth embodiment of the present invention will now be described. This embodiment concerns with specifying a three-dimensional ROI for producing MPR (multi-planar reconstruction) images based on the ROI.

FIG. 13 explains how to process original images in the present embodiment, while FIG. 14 shows an outlined flow of processing carried out using the user interface (i.e., the host computer 6, display 12, and input device 13).

First, in response to an operator's command, the host computer 6 operates such that three-dimensional (3D) image data is obtained by actually scanning an object P (patient) in, for example, a multi-slice technique or reading out 3D image data that has already been acquired and stored in the storage 11 or other memory means, like the PACS (step S71 in FIG. 14). This 3D image data, which is composed of data of a plurality of sections P41 to P4$n$, is temporarily stored as original 3D image data in a work area of the host computer 6 (refer to FIG. 13).

Using the user interface, a spherical ROI serving as the three-dimensional ROI is then specified at a desired region to be subjected to MPR processing in the original 3D images (step S72). A direction along which the MPR processing is carried out for the data contained in the spherical ROI is then specified (step S73).

Based on the specified MPR direction, the MPR processing is performed through the synthesis of image data surrounded by the spherical ROI (step S74), so that new image data of sections P51 to P5$m$ located in a depth range defined by the diameter of the spherical ROI are re-produced. Locations and/or intervals of sections P51 to P5$m$ to be subjected to the MPR processing can be designated in advance, if required. The sections P51 to P5$m$ cross the spherical ROI.

Finally, of the MPR images, one or more images are displayed by display 12, as exemplified in FIG. 13.

Hence, the way of specifying the three-dimensional ROI can also be used for producing MPR images. Since the re-production of data of new images (i.e., synthesis of original image data) and display thereof can be taken successively, with the result that, compared to the conventional MPR technique, the step to search desired MPR images from a large number of MPR-processed images can be omitted. This will simplify the processing required for the MPR and shorten the time required for the MPR.

In the foregoing embodiments, the user interface used for specifying and locating the three-dimensional ROI (for example, spherical ROI) a desired region in images is integrated in the MRI system, but this is not a definitive list. Alternatively, a processing apparatus, such as workstation or PC (personal computer), dedicated to the foregoing image processing and image display may be used.

As to the medical imaging modality, the example described in the foregoing embodiments is not a definitive list. The medical imaging modality may be an X-ray CT scanner or others, not limited to the MRI system.

For the sake of completeness, it should be mentioned that the embodiment explained so far is not a definitive list of possible embodiments of the present invention. The expert will appreciate that it is possible to combine the various construction details or to supplement or modify them by measures known from the prior art without departing from the basic inventive principle.

The entire disclosure of Japanese Patent Application No.2002-235823 filed on Aug. 13, 2002 including the specification, claims, drawings and summary is incorporated herein by reference in its entirety.

What is claimed is:

1. An apparatus for image processing comprising a computer system including:
    a storage unit configured to store a plurality of previously acquired different types of diagnostic tomographic images of an object to be diagnosed;
    a display unit configured to display tomographic images of the object having different orientations;
    a ROI-specifying unit configured to specify a three-dimensional ROI (region of interest) at a region to be targeted for viewing in a three-dimensional space formed by the tomographic images; and
    a search unit configured for accessing the previously acquired diagnostic images of different types stored in the storage unit to search one or more images for image data included in the specified three-dimensional ROI and for storing or outputting image data found within said ROI.

2. The apparatus of claim 1, wherein the search unit comprises a deciding unit configured to decide which one or more sections of the plurality of the searched images cross the specified three-dimensional ROI; and a searched-image display unit configured to display at least part of the sections identified by the deciding unit.

3. The apparatus of claim 2, wherein the searched-image display unit is configured to display images of the sections identified by the deciding unit, the image of each of the identified sections including an area crossing the three-dimensional ROI being superposed on each image.

4. The apparatus of claim 1, wherein the search unit comprises a unit configured to search the plurality of images for sections crossing the three-dimensional ROI and to identify a contour of the area crossing the three-dimensional ROI in each of the identified sections.

5. The apparatus of claim 1, wherein the ROI-specifying unit comprises:

a ROI-placing unit configured to place the three-dimensional ROI at the region to be targeted on an image of a first section selected from the plurality of sections; and a ROI-locating unit configured to three-dimensionally locate the three-dimensional ROI at the region to be targeted by using both the image and a second image of section from the plurality of sections.

6. The apparatus of claim 5, wherein the first image is a sagittal image of the object and the second image is a coronal image of the object.

7. The apparatus according to claim 5, further comprising:

an image/ROI display unit configured to display at least one of the first and second images together with the three-dimensional ROI superposed thereon.

8. The apparatus of claim 7, wherein both the ROI-placing unit and the ROI-locating unit are configured to allow an operator to manually define the three-dimensional ROI on the first and second images.

9. The apparatus of claim 5, wherein the first and second sections are perpendicular to each other.

10. The apparatus of claim 1, wherein the three-dimensional ROI has a fixed shape to define a contour thereof.

11. The apparatus of claim 10, wherein the three-dimensional ROI is a spherical ROI.

12. The apparatus of claim 11, functionally incorporated in a medical imaging modality for acquiring the plurality of images at the plurality of sections.

13. The apparatus of claim 12, wherein the medical imaging modality is one selected from a group of medical imaging modalities including an MRI (magnetic resonance imaging) system and an X-ray CT (computed tomography) scanner.

14. The apparatus of claim 1, wherein the plurality of images stored in the storage unit and subjected to search include MR (magnetic resonance) images and CT (X-ray computed tomography) images both of which are acquired from the same object.

15. The apparatus of claim 1, wherein the plurality of images stored in the storage unit and subjected to search include a plurality of images acquired by imaging and/or a plurality of images acquired from outside the system via a network.

16. The apparatus of claim 1, wherein the plurality of images subjected to the search include a plurality of sagittal images of the object.

17. The apparatus of claim 1, wherein the plurality of images subjected to the search are a sagittal image of the object and an axial image of the object.

18. A method for image processing in a computer system a plurality of different types of previously acquired diagnostic images stored in a storage unit of an object to be diagnosed, the method comprising use of a computer system for:

displaying tomographic images of the object having different respective orientations;

specifying a three-dimensional ROI (region of interest) at a region to be targeted for viewing;

searching said different types of images based on image data stored in a storage unit for one or more images having image data included in the three-dimensional ROI; and storing or outputting image data found within said ROI.

19. The method of claim 18, wherein:

the search step includes a step of deciding whether one or more sections of a plurality of sections cross the three-dimensional ROI and a step of displaying, as the one or more searched images, at least part of the images of the sections found to cross the ROI; and the display step is configured to display at least part of the images of the sections identified by the deciding step, the image of each of the identified sections including an area crossing the three-dimensional ROI superposed on each image.

20. The method of claim 19, wherein the display step comprises the sub-steps of:

searching the plurality of images for sections crossing the three-dimensional ROI; and deciding whether a contour of the area crosses the three-dimensional ROI in each of the thus identified sections.

21. A program storage medium storing a computer program which, when executed by a computer for image processing a plurality of previously acquired different types of diagnostic images of an object to be diagnosed stored in a storage unit, the program enables the computer to perform a method comprising:

displaying tomographic images of the object having different respective orientations;

specifying a three-dimensional ROI (region of interest) at a region to be targeted for viewing in a three-dimensional space formed by the tomographic images;

searching stored image data for one or more images to having image data included in the three-dimensional ROI; and storing or outputting image data found within said ROI.

22. The program of claim 21, wherein:

the search step includes a step of deciding whether one or more sections of a plurality of images crosses the specified three-dimensional ROI and a step of displaying, as the one or more searched images, at least part of the images of the sections identified during the search; and the display step is configured to display images of the sections identified by the deciding step, the image of each of the identified sections including an area crossing the three-dimensional ROI superposed on each image.

23. The method of claim 22, wherein the display step comprises the sub-steps of:

searching the plurality of images for sections crossing the three-dimensional ROI; and deciding whether a contour of the area crosses the three-dimensional ROI in each of the identified sections.

24. A magnetic resonance imaging (MRI) system comprising a computer system including:

an imaging device configured to acquire data from an object, the data being generated by magnetic resonance induced inside the object;

a reconstruction device configured to reconstruct the acquired data into a plurality of different types of diagnostic images;

a storage unit configured to store the plurality of reconstructed diagnostic images; and an image processor comprising;

a display unit configured to display diagnostic tomographic images of the diagnostic object, the tomographic images having different orientations;

a ROI-specifying unit configured to specify a three-dimensional ROI (region of interest) at a region to be targeted for viewing in a three-dimensional space formed by the diagnostic tomographic images; and a search unit configured to search for one or more images having image data included in the three-dimensional ROI from among the plurality of reconstructed diagnostic images stored in the storage unit and to store or output image data found within said ROI.

25. The system of claim 24, wherein the search unit comprises a deciding unit configured to identify one or more sections of a plurality of crossing the three-dimensional ROI; and a searched-image display unit configured to display at least part of the images of the sections identified by the deciding unit.

26. The system of claim 25, wherein the searched-image display unit is configured to display images of the sections identified by the deciding unit, the image of each of the identified sections including an area crossing the three-dimensional ROI superposed on each image.

27. The apparatus of claim 24, wherein the ROI-specifying unit comprises a ROI-placing unit configured to place the three-dimensional ROI at the region to be targeted on a first image of a first section selected from the plurality of sections; and a ROI-locating unit configured to three-dimensionally locate the three-dimensional ROI at the region to be targeted by using both the first image and a second image of a second section from the plurality of sections.

28. The system of claim 27, further comprising:

an image/ROI display unit configured to display at least one of the first and second images together with the three-dimensional ROI superposed thereon.

29. The system of claim 28, wherein both the ROI-placing unit and the ROI-locating unit are configured to allow an operator to manually locate the three-dimensional ROI on the first and second images.

30. The system of claim 27, wherein the first and second sections are perpendicular to each other.

31. The system of claim 27, wherein the first image is a sagittal image of the object and the second image is a coronal image of the object.

32. The system of claim 24, wherein the search unit comprises a unit configured to search the plurality of images for images crossing the three-dimensional ROI and to identify a contour of the area crossing the three-dimensional ROI in each of the identified sections.

33. The system of claim 24, wherein the three-dimensional ROI has a fixed shape to define a contour thereof.

34. The system of claim 33, wherein the three-dimensional ROI is a spherical ROI.

35. The system of claim 24, wherein the search unit is configured to be active after the imaging device acquires the data from the object, the reconstruction device reconstructs the acquired data into the plurality of images, and the storage unit stores the plurality of images reconstructed.

36. The system of claim 24, wherein the plurality of images stored in the storage unit and subjected to search include a plurality of images acquired by imaging and/or a plurality of images acquired from outside the system via through a network.

37. The system of claim 24, wherein the plurality of images subjected to the search include a plurality of sagittal images of the object.

38. The system of claim 24, wherein the plurality of images subjected to the search are a sagittal image of the object and an axial image of the object.

* * * * *